(12) United States Patent
Connolly et al.

(10) Patent No.: US 10,729,884 B2
(45) Date of Patent: Aug. 4, 2020

(54) GUIDE EXTENSION CATHETER WITH HELICALLY-SHAPED ENTRY PORT

(71) Applicant: Medtronic Vascular, Inc., Santa Rosa, CA (US)

(72) Inventors: Colm Connolly, Galway (IE); Patrick Griffin, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 472 days.

(21) Appl. No.: 15/479,327

(22) Filed: Apr. 5, 2017

(65) Prior Publication Data
US 2017/0296783 A1 Oct. 19, 2017

Related U.S. Application Data

(60) Provisional application No. 62/322,309, filed on Apr. 14, 2016.

(51) Int. Cl.
*A61M 25/01* (2006.01)
*A61M 25/00* (2006.01)
(Continued)

(52) U.S. Cl.
CPC .... *A61M 25/0102* (2013.01); *A61M 25/0052* (2013.01); *A61M 25/0662* (2013.01);
(Continued)

(58) Field of Classification Search
CPC .. A61M 2025/0004; A61M 2025/0681; A61M 2025/09191; A61M 25/0102;
(Continued)

(56) References Cited

U.S. PATENT DOCUMENTS

2009/0264865 A1 10/2009 Kawai
2010/0217237 A1* 8/2010 Itou .................. A61B 17/22
604/540
(Continued)

FOREIGN PATENT DOCUMENTS

EP 1639951 3/2006
WO WO2013/185148 12/2013

OTHER PUBLICATIONS

PCT/US2017/026213, The International Search Report and the Written Opinion of the International Searching Authority, dated Jun. 22, 2017.

*Primary Examiner* — Rebecca E Eisenberg
*Assistant Examiner* — Tasnim Mehjabin Ahmed
(74) *Attorney, Agent, or Firm* — Shumaker & Sieffert, P.A.

(57) ABSTRACT

A guide extension catheter includes a push member and a distal shaft coupled to and extending distally from the push member. The distal shaft includes a shaft wall and a passageway. The shaft wall includes a helically-shaped proximal end and a distal end. The helically-shaped proximal end coils helically about a first central longitudinal axis of the passageway of the distal shaft. The helically-shaped proximal end of the shaft wall defines a helically-shaped entry port of the distal shaft. The distal shaft may include a helically-shaped collar coupled to the helically-shaped proximal end of the distal shaft, the collar defining the helically-shaped entry port of the distal shaft.

10 Claims, 8 Drawing Sheets

(51) Int. Cl.
*A61M 25/06* (2006.01)
*A61M 25/09* (2006.01)

(52) U.S. Cl.
CPC ..... *A61M 25/09* (2013.01); *A61M 2025/0004* (2013.01); *A61M 2025/0681* (2013.01); *A61M 2025/09191* (2013.01); *A61M 2205/0266* (2013.01)

(58) Field of Classification Search
CPC ............ A61M 25/005; A61M 25/0052; A61M 25/0068; A61M 25/0662; A61M 25/09
See application file for complete search history.

(56) References Cited

U.S. PATENT DOCUMENTS

| | | |
|---|---|---|
| 2013/0116701 A1 | 5/2013 | Wang et al. |
| 2013/0237962 A1* | 9/2013 | Kawai ............... A61M 25/0102 604/524 |
| 2014/0052097 A1* | 2/2014 | Petersen ............... A61M 25/01 604/506 |
| 2014/0276618 A1* | 9/2014 | Di Caprio ......... A61M 25/0068 604/510 |
| 2016/0008572 A1 | 1/2016 | DiCaprio et al. |
| 2016/0051799 A1 | 2/2016 | Daniels et al. |

\* cited by examiner

GUIDE EXTENSION CATHETER WITH HELICALLY-SHAPED ENTRY PORT

CROSS-REFERENCE TO RELATED APPLICATIONS

This application claims the benefit under 35 U.S.C. § 119(e) of the filing date of U.S. Provisional Application No. 62/322,309 filed Apr. 14, 2016, the contents of which are incorporated by reference herein in their entirety.

FIELD OF THE INVENTION

The present invention relates to a guide extension catheter for use with a guide catheter. More particularly, the present invention relates to a guide extension catheter with a helically-shaped entry port providing easier entry of coronary devices into the distal shaft of the guide extension catheter.

BACKGROUND

Arteries of the heart, and more specifically coronary arteries, may sometimes be occluded or narrowed by atherosclerotic plaques or other lesions. These afflictions are generally referred to as coronary heart disease or a stenosis, and result in inadequate blood flow to distal arteries and tissue. Heart bypass surgery may be a viable surgical procedure for certain patients suffering from coronary heart disease. However, attendant with traditional open surgery, significant patient trauma, discomfort, extensive recuperation times, and life threatening complications may occur due to the invasive nature of the surgery and the necessity for stoppage of the heart during such a surgery.

To address these concerns, efforts have been made to perform interventional cardiology procedures using minimally invasive techniques. In certain efforts, percutaneous transcatheter (or transluminal) delivery and implantation of interventional coronary devices are employed to solve the problems presented by traditional open surgery. Typically, a guide catheter is first inserted through an incision into a femoral (transfemoral), or radial (transradial) artery of a patient. Transradial access is increasingly accepted as a method offering lower post-operative bleeding complications and quicker recovery times for patients. However the smaller diameter of the radial artery requires a smaller diameter guide catheter. The smaller diameter guide catheter has less back support than a similarly configured femoral guide catheter. For example, the Seldinger technique may be utilized in either method for percutaneously introducing the guide catheter. In such methods, the guide catheter is advanced through the aorta and inserted into the opening of an ostium of a coronary artery. A guidewire, or other interventional coronary devices such as a catheter mounted stent and/or balloon catheter, may be introduced through the guide catheter and maneuvered/advanced through the vasculature and the stenosis of the diseased coronary artery. However, when attempting to pass through a difficult stenosis, or when conducting a radial intervention using a small diameter guide catheter, the guide catheter may not have adequate back support, and continued application of force to advance the interventional device though the stenosis may cause the distal end of the guide catheter to dislodge from the opening of the ostium of the coronary artery, resulting in potential damage to the surrounding tissue.

In order to prevent the guide catheter from dislodging, interventional cardiologists sometimes would deep seat the guide catheter into the coronary artery. The term "deep seat" or "deep seating" means that the guide catheter would be pushed farther downstream into the coronary artery. However, deep seating the guide catheter risks the guide catheter damaging the coronary artery wall (dissection or rupture), occluding the coronary artery, and interfering with blood flow to the coronary artery.

One attempt to provide additional back support to a guide catheter that has gained acceptance is the use of a guide extension catheter. The guide extension catheter is deployed within a lumen of the guide catheter and extends distally from the distal end of the guide catheter into the coronary artery. Their smaller size, as compared to the guide catheter, allows the guide extension catheter to be seated more deeply in the coronary artery with less potential damage. This provides additional back support to the guide catheter to aid in delivery of interventional coronary devices. In cases with a difficult stenosis or radial interventions, the use of the guide extension catheter reduces the risk of dislodging the guide catheter from the opening of the ostium of the coronary artery during treatment. However, with their smaller size, guide extension catheters may pose difficulty in receiving an interventional coronary device within the passageway of the distal shaft of the guide extension catheter. As an example, an interventional coronary device such as a catheter with a stent mounted on an outer surface of a balloon may catch, snag, or otherwise become snared on the entry port of the distal shaft of the guide extension catheter. While efforts have been made to ease the introduction of interventional coronary devices into the passageway of the distal shaft of the guide extension catheter by angling or skiving the entry port of the distal shaft, these methods are only in a single plane and have not eliminated the instances of catching and snagging of interventional coronary devices on the entry port of the distal shaft of guide extension catheters.

Accordingly, there exists a need for an improved guide extension catheter distal shaft entry port design that provides easier entry into the passageway of the distal shaft and reduces catching and snagging of interventional coronary devices advancing into the passageway of the distal shaft.

SUMMARY OF THE INVENTION

Embodiments hereof relate to a guide extension catheter including a push member and a distal shaft coupled to and extending distally from the push member. The distal shaft includes a shaft wall and a passageway. The shaft wall includes a helically-shaped proximal end and a distal end. The helically-shaped proximal end coils helically about a first central longitudinal axis of the passageway of the distal shaft. The helically-shaped proximal end of the shaft wall defines a helically-shaped entry port of the distal shaft. The distal shaft may include a helically-shaped collar coupled to the helically-shaped proximal end of the distal shaft, the collar defining the helically-shaped entry port of the distal shaft.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION

Specific embodiments of the present invention are now described with reference to the figures, wherein like reference numbers indicate identical or functionally similar elements. The terms "distal" and "proximal", when used in the following description to refer to a guidewire, catheter, and/or other system components hereof are with respect to a position or direction relative to the treating clinician. Thus, "distal" and "distally" refer to positions distant from, or in a direction away from the treating clinician, and the terms "proximal" and "proximally" refer to positions near, or in a direction toward the clinician. The terms "distal" and "proximal", when used in the following description to refer to a native vessel or native valve are used with reference to the direction of blood flow. Thus, "distal" and "distally" refer to positions in a downstream direction with respect to the direction of blood flow and the terms "proximal" and "proximally" refer to positions in an upstream direction with respect to the direction of blood flow.

The following detailed description is merely exemplary in nature and is not intended to limit the invention or the application and uses of the invention. Furthermore, there is no intention to be bound by any expressed or implied theory presented in the preceding technical field, background, brief summary, or the following detailed description.

FIGS. 1-5 illustrate a guide extension catheter 100 in accordance with an embodiment hereof. The guide extension catheter 100 includes a push member 102 coupled to a distal shaft 104. The push member 102 is coupled to the distal shaft 104 at a transition joint 103.

Figure 1:
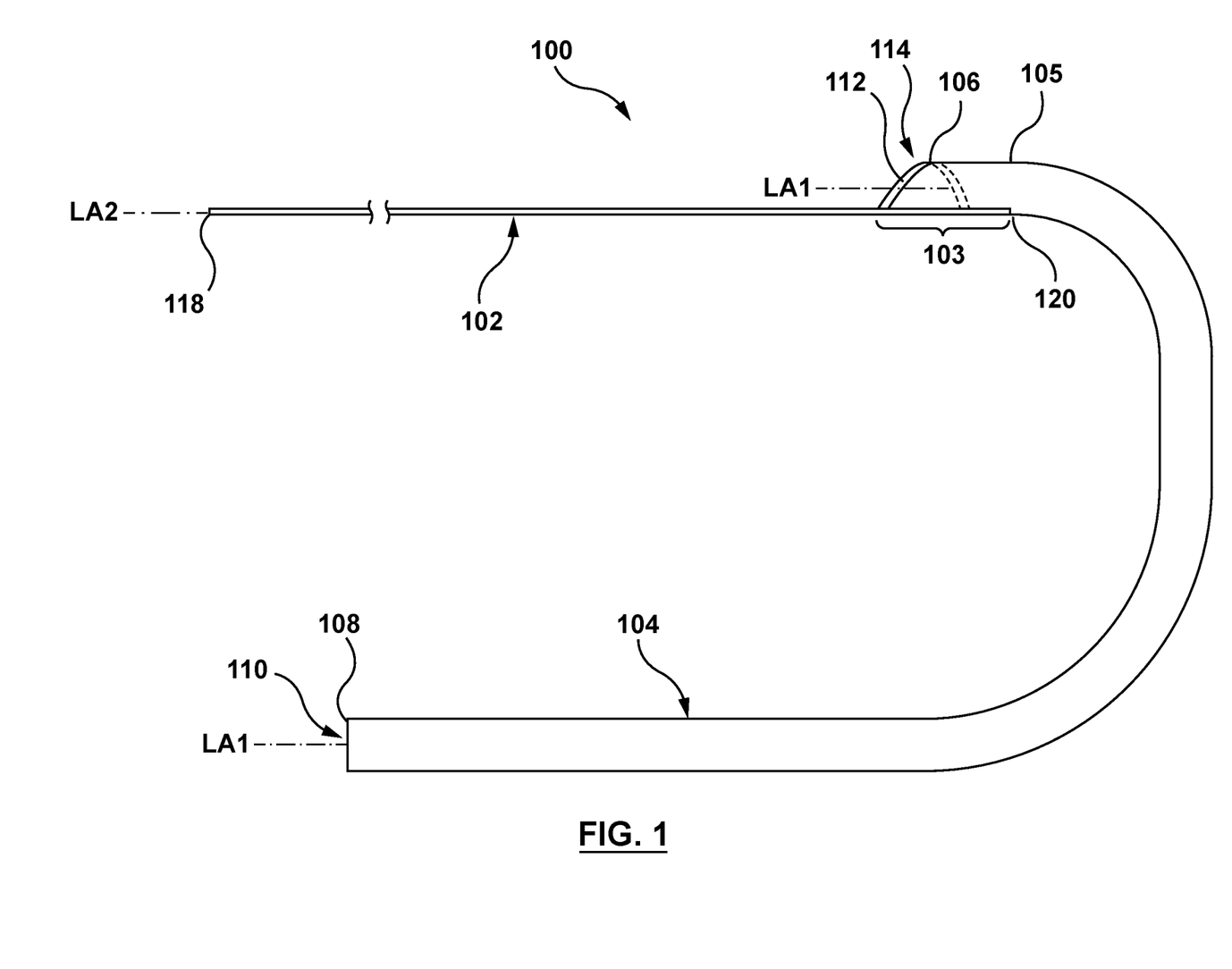
FIG. 1 is a side view illustration of a guide extension catheter in accordance with an embodiment hereof.

The push member 102, which may also be referred to as a proximal shaft, may be a wire, hypotube, shaft, partial shaft, or other configurations suitable for the purposes described herein. The push member 102 includes a proximal end 118 and a distal end 120, as shown in FIG. 1. A distal portion of the push member 102 is coupled to a proximal portion of the distal shaft 104 at the transition joint 103. The push member 102 is configured to transfer motion applied at the proximal end 118 to the distal end 120, which is coupled to the distal shaft 104 at the transition joint 103. Therefore, the push member 102 is further configured to transfer motion at the proximal 118 to the transition joint 103 through the distal end 120, and to the distal shaft 104 through the transition joint 103. The push member 102 may be formed of materials such as, but not limited to stainless steel, nickel-titanium alloys (e.g. NITINOL), high performance alloys that at cobalt, chromium, molybdenum and/or nickel based (e.g., MP35N, L605, ELGILOY), or other materials suitable for the purposes disclosed herein.

In an embodiment, the transition joint 103 includes a proximal portion of the distal shaft 104 and a distal portion of the push member 102. In an embodiment, the transition joint 103 is formed by overlapping the distal portion of the push member 102 and the proximal portion of the distal shaft 104, as shown in FIG. 1. The transition joint 103 is configured to couple the push member 102 to the distal shaft 104 such that motion of the push member 102 is transferred to the distal shaft 104. The transition joint 103 is further configured to act as an exchange joint such that interventional coronary devices may be advanced into a passageway 110 of the distal shaft 104 of the guide extension catheter 100 as described in greater detail below.

Figure 2:
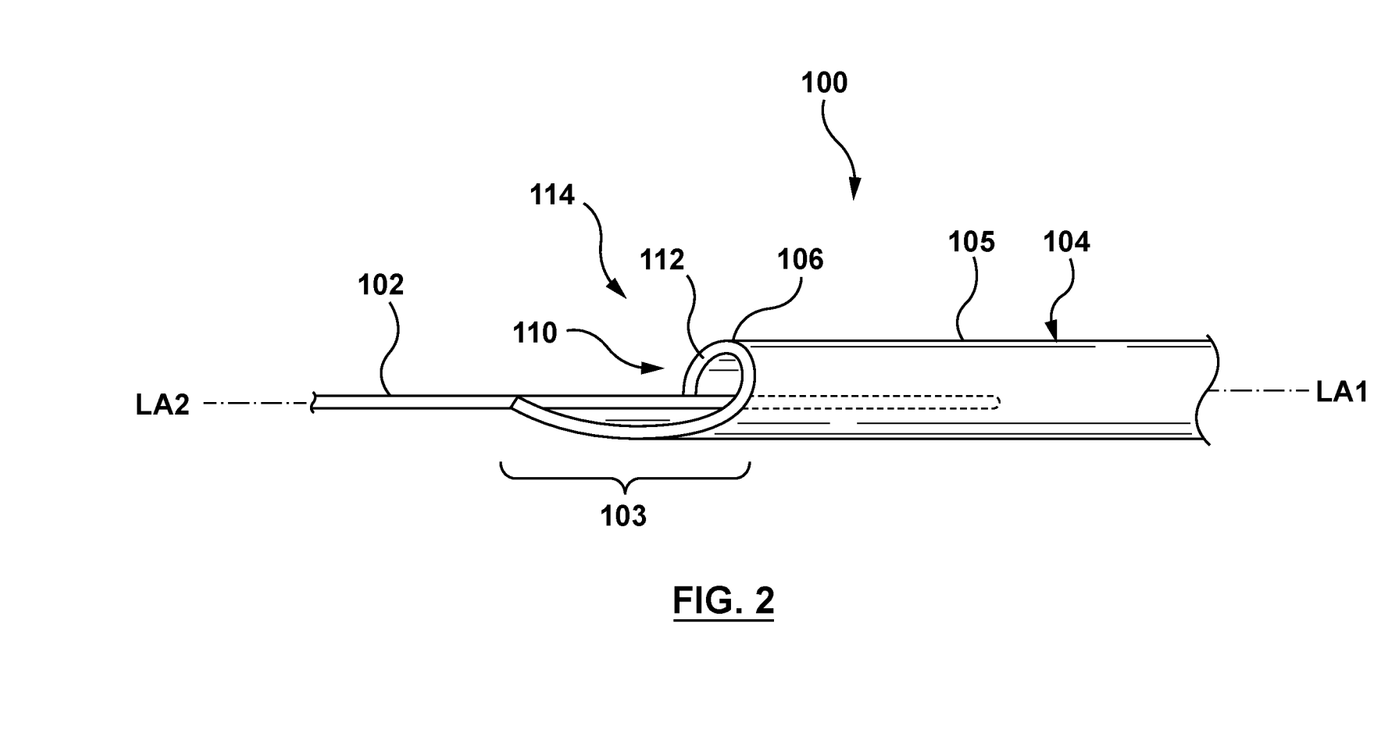
FIG. 2 is a perspective illustration of the guide extension catheter of FIG. 1.

In an embodiment, the distal shaft 104 includes a shaft wall 105 and the passageway 110, as shown in FIGS. 1-2. The shaft wall 105 of the distal shaft 104 extends distally from a proximal end 106 to a distal end 108. The proximal end 106 of the shaft wall 105 is helically-shaped around a first central longitudinal axis LA1 of the distal shaft 104. The distal shaft 104 further includes a collar 112 coupled to the helically-shaped proximal end 106 of the shaft wall 105 of the distal shaft 104. The collar 112 is helically-shaped to match the helical shape of the proximal end 106 of the shaft wall 105. The collar 112 is coupled to the proximal end 106 of the shaft wall 105 such that the collar 112 and the proximal end 106 together define a helically-shaped entry port 114 of the distal shaft 104. The collar 112 may be a wire or a ribbon, or other shape suitable for the purposes described herein. The collar 112 may be formed of materials such as, but not limited to stainless steel, nickel-titanium alloys (e.g. NITINOL), or other suitable materials. The collar 112 may be coupled to the helically-shaped proximal end 106 of the shaft wall 105 of the distal shaft 104 by methods such as, but not limited to adhesives, fusing, welding, bonding, mechanical connections, or any other method suitable for the purposes described herein.

Figure 3:
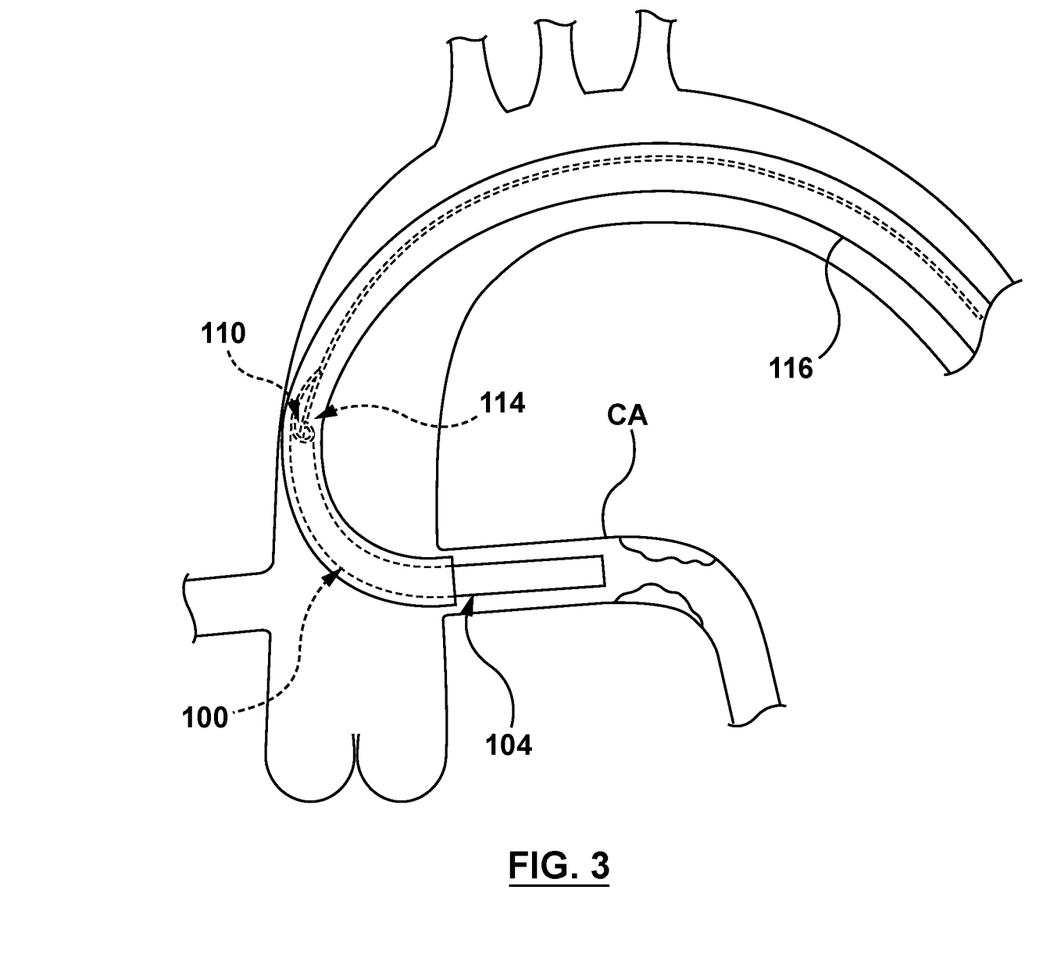
FIG. 3 is a side view illustration of the guide extension catheter of FIG. 1 extending through a guide catheter and disposed within a coronary artery.

The guide extension catheter 100 is configured for advancement through a guide catheter 116, as shown in FIG. 3. The guide extension catheter 100 is further configured to be seated within a coronary artery CA such that the guide extension catheter 100 provides additional back support to the guide catheter 116. The guide extension catheter 100 is even further configured such that the helically-shaped entry port 114 of the distal shaft 104 provides easy entry of an interventional coronary device to the passageway 110 of the distal shaft 104. More specifically, the helically-shaped entry port 114 provides easier entry into the passageway 110 than angled or circular entry ports, thereby reducing catching and/or snagging of interventional coronary devices entering the passageway 110 of the distal shaft 104. Non-limiting examples of interventional coronary devices include guidewires, balloon catheters, stent catheters, and FFR catheters. In an embodiment, the guide extension catheter 100 may be approximately 150 cm in length, with the distal shaft 104 of the guide extension catheter 100 being between 20 cm and 40 cm in length. However, this is not meant to limit the design and the guide extension catheter 100 and/or the distal shaft 104 thereof may be longer or shorter.

Figure 4:
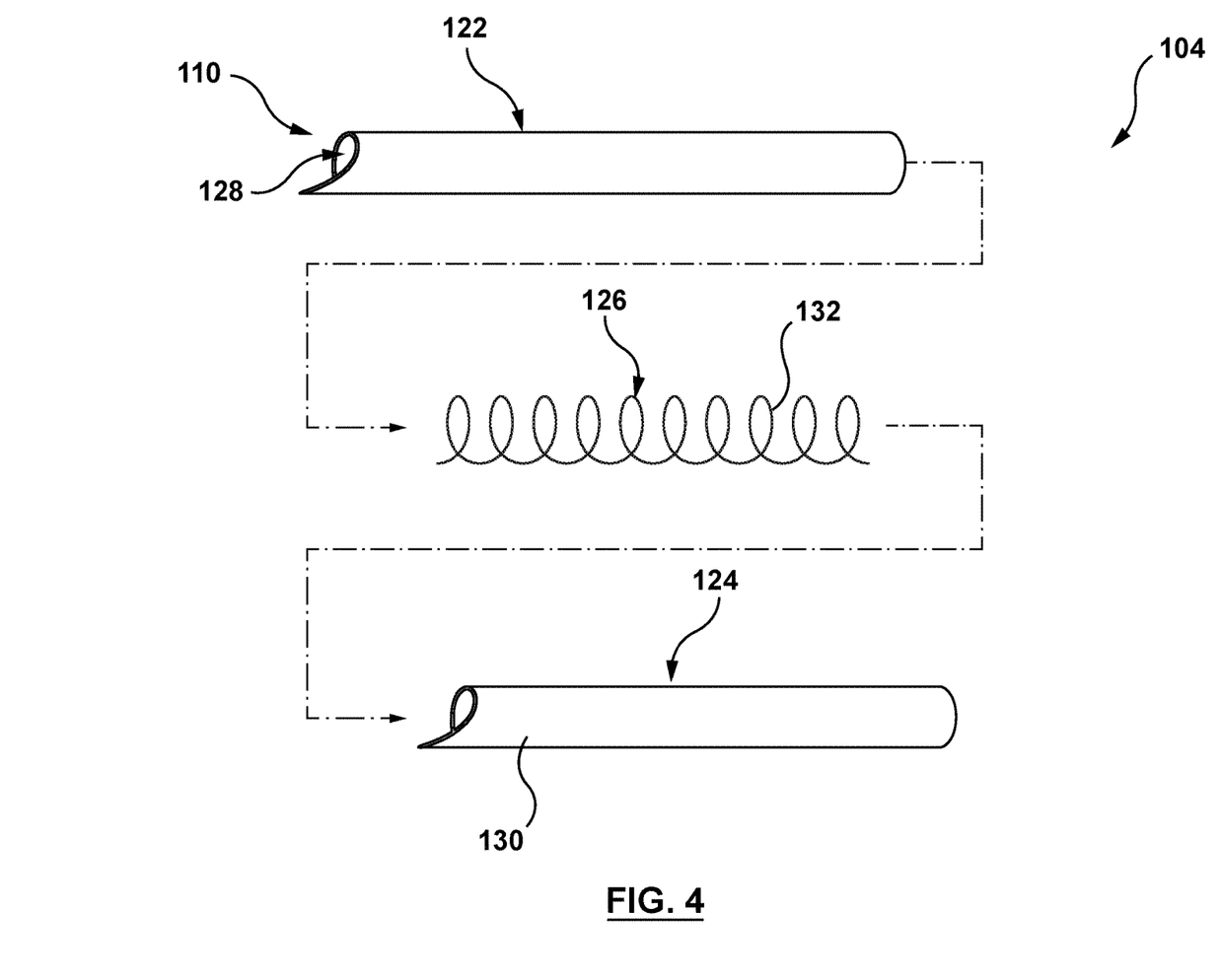
FIG. 4 is an exploded perspective illustration of an embodiment of a distal shaft of the guide extension catheter of FIG. 1.

The distal shaft 104 of the guide extension catheter 100 may be constructed of various materials, non-limiting examples of which include a polymer hypotube, a braided polymer hypotube, or a layered hypotube. In an example, the distal shaft 104 may include an inner liner 122, an outer jacket 124 and a support structure 126, as shown in of FIG. 4. The inner liner 122 of the distal shaft 104 is of a generally tubular shape and forms an inner surface 128 of the distal shaft 104. The inner liner 122 is configured to provide the distal shaft 104 with a low friction inner surface such that interventional coronary devices may be advanced/retracted easily through the passageway 110 of the distal shaft 104. The inner liner 122 may be formed from materials such as, but not limited to polytetrafuoroethylene (PTFE), perfluoroalkoxy alkanes (PFAs), high-density polyethylene (HDPA), or other materials suitable for the purposes described herein. The outer jacket 124 of the distal shaft 104 is of a generally tubular shape and forms an outer surface 130 of the distal shaft 104, as shown in FIG. 4. The outer jacket 124 is configured to provide flexibility to the distal shaft 104. The outer jacket 124 may be formed from materials such as, but not limited to, thermoplastic elastomers, such as but not limited to polyether block amides (e.g. PEBAX®, VESTAMID®), nylon, or other materials suitable for the purposes described herein. The support structure 126 of the distal shaft 104 is a generally tubular helically wound wire member 132 (also known as a filament). In the example of FIG. 4, the helical coil support structure 126 is embedded between the inner liner 122 and the outer jacket 124. The support structure 126 is configured to provide strength and rigidity to the distal shaft 104. The support structure 126 may be bonded between the inner liner 122 and the outer jacket 124 by methods such as, but not limited to heat, fusion, adhesives, or other suitable methods. The support structure 126 may be formed from materials such as, but not limited to, stainless steel, nickel-titanium alloys (e.g. NITINOL), or other materials suitable for the purposes described herein.

Figure 5:
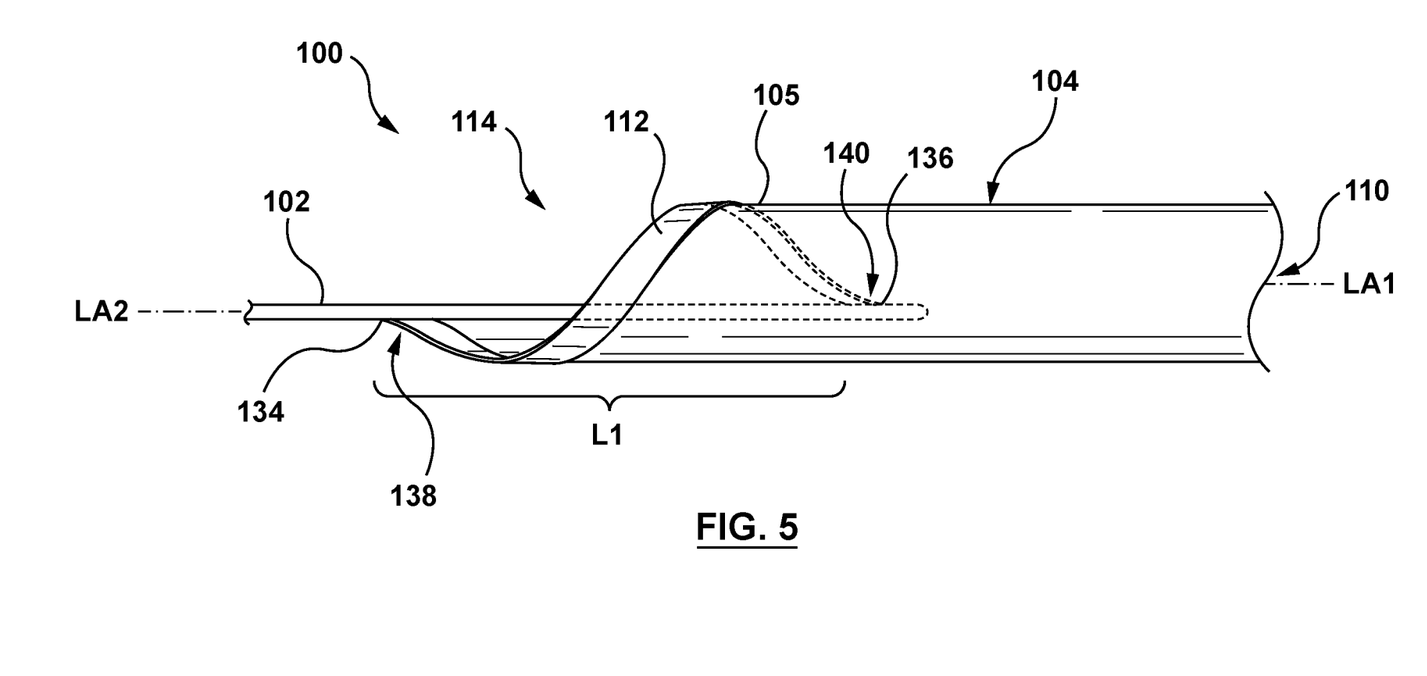
FIG. 5 is a perspective illustration of a portion of the guide extension catheter of FIG. 1.

FIG. 5 is a close-up perspective illustration of the distal portion of the push member 102 and the proximal portion of the distal shaft 104 of the guide extension catheter 100 of FIGS. 1-2. Referring to FIG. 5, the collar 112 in this embodiment is a ribbon with a generally rectangular cross-sectional profile (although it could alternatively be a wire with a circular, elliptical, oval, or other cross-section). The collar 112 includes a proximal end 134 and a distal end 136 longitudinally offset from each other by a length L1 along a portion of distal shaft 104. The length L1 is measured along a second central longitudinal axis LA2 of the push member 102. The proximal end 132 of the collar 112 is tapered in shape and is coupled to the push member 102 at a proximal joint 138. In an embodiment, the distal end 136 of the collar 112 is tapered in shape and is coupled to the push member 102 at a distal joint 140. The proximal and distal ends 132, 134 of the collar 112 may be coupled to the push member 102 at the proximal joint 138 and the distal joint 140, respectively, by methods such as, but not limited to adhesives, fusing, welding, bonding, mechanical connection, or any other method suitable for the purposes described herein.

Figure 6:
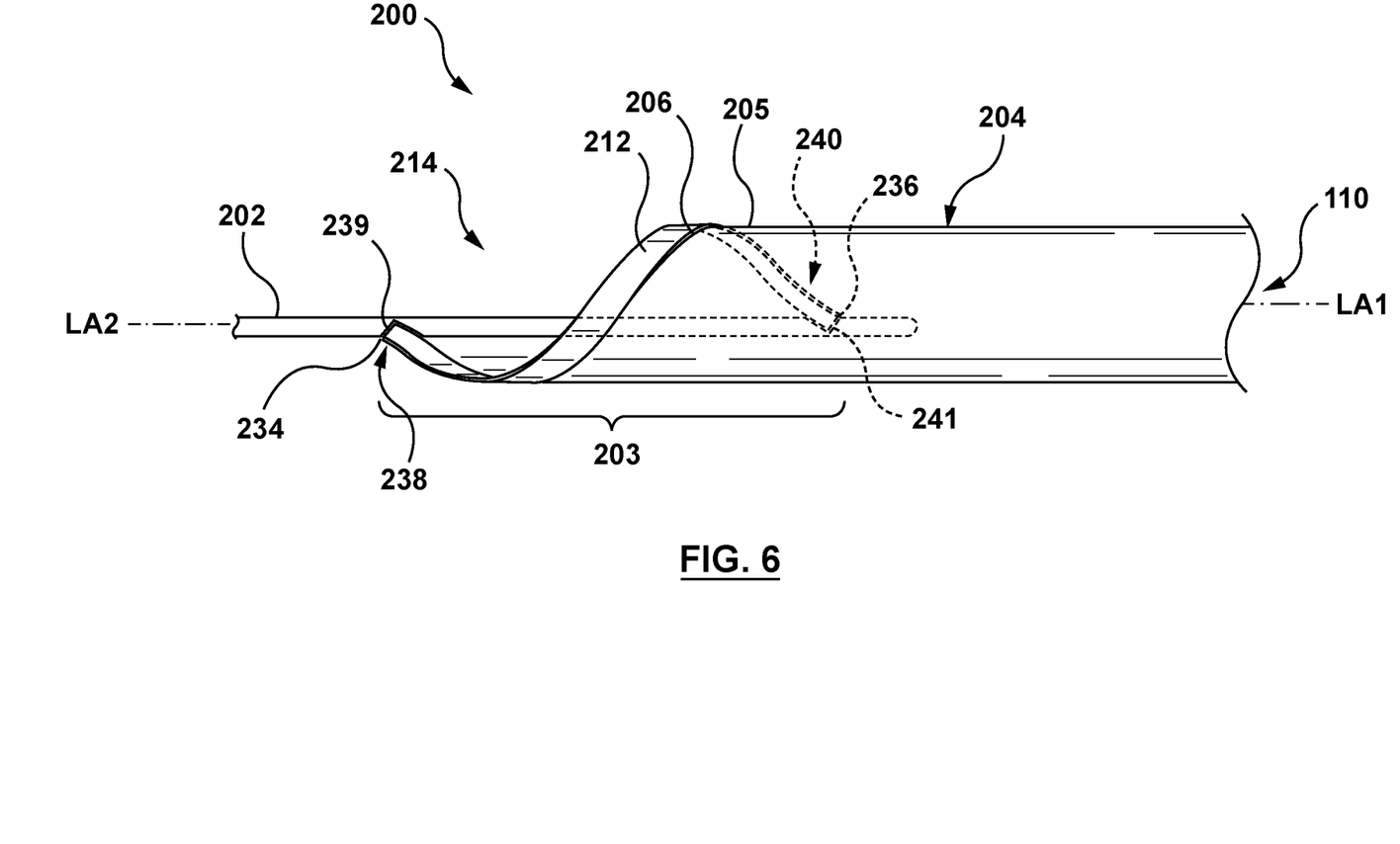
FIG. 6 is a perspective illustration of a portion of a guide extension catheter in accordance with another embodiment hereof.

FIG. 6 illustrates a guide extension catheter 200 with a helically-shaped entry port 214 according to another embodiment hereof. The guide extension catheter 200 includes a push member 202, a distal shaft 204, a transition joint 203, a passageway 210, and a helically-shaped collar 212 coupled to a helically-shaped proximal end 206 of a shaft wall 205 of the distal shaft 204. The guide extension catheter 200 is similar to the guide extension catheter 100, described previously. Accordingly, the push member 202, the distal shaft 204, the transition joint 203, the passageway 210, the collar 212 and the helically-shaped entry port 214 are similar to the push member 102, the distal shaft 104, the transition joint 103, the passageway 110, the collar 112 and the helically-shaped entry port 114 described previously. Therefore, details of their construction and alternatives will not be repeated. Similarly, the collar 212 of the guide extension catheter 200 is coupled to the push member 202 at a proximal joint 238 and a distal joint 240. However, in the embodiment of FIG. 6, the proximal joint 238 includes a proximal skive 239 in the push member 202 and the distal joint 240 includes a distal skive 241 in the push member 202. The term "skive" as utilized herein refers to an angled notch or opening formed in a surface of the push member 202. In an embodiment, the proximal skive 239 and the distal skive 241 may each be formed by a skiving or scarfing process, or other processes suitable for the purposes disclosed herein. In the embodiment shown in FIG. 6, the collar 212 is a wire with a generally circular cross-sectional profile (although it may alternatively be a ribbon or a wire with a different shape cross-sectional profile (e.g. elliptical). The collar 212 includes a proximal end 234 disposed within and coupled to the proximal skive 239 of the push member 202, and a distal end 236 disposed within and coupled to the distal skive 241 of the push member 202. The collar 212 is coupled to the push member 202 within the proximal skive 239 and the distal skive 241 by methods such as, but not limited to adhesives, fusing, welding, bonding, mechanical connection, or any other method suitable for the purposes described herein.

Figure 7:
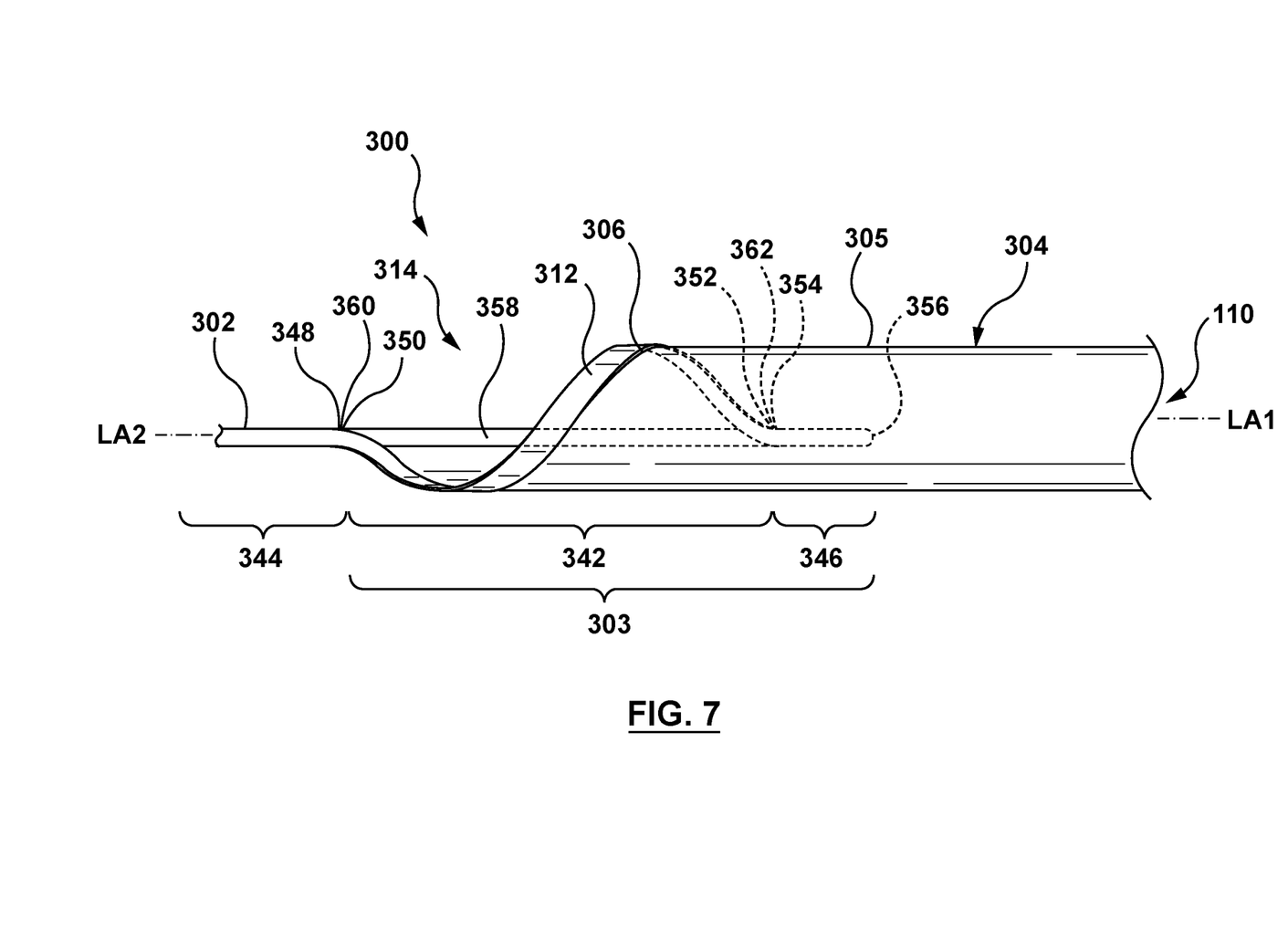
FIG. 7 is a perspective illustration of a portion of a guide extension catheter in accordance with another embodiment hereof.

FIG. 7 illustrates a guide extension catheter 300 with a helically-shaped entry port 314 according to yet another embodiment hereof. The guide extension catheter 300 includes a push member 302, a distal shaft 304, a transition joint 303, a passageway 310, a helically-shaped collar 312 coupled to a helically-shaped proximal end 306 of a shaft wall 305 of the distal shaft 304, and a push member extension 358 coupled at its ends to the push member 302. The guide extension catheter 300 and its components are similar to the guide extension catheter 100 and its components, described previously, and therefore are not described in detail with respect to FIG. 7. However, in the embodiment of FIG. 7, the collar 312 is formed by deviating a central portion 342 of the push member 302 from a second longitudinal axis LA2 and helically wrapping the central portion 342 around a first longitudinal axis LA1. Additionally, the push member extension 358 is coupled at a proximal end 360 thereof to the push member 302 at a location where the push member 302 begins to deviate from the second longitudinal axis LA2. The push member 358 is also coupled at a distal end 362 thereof to the push member 302 at a location where the push member 302 returns to the second longitudinal axis LA2, as described in more detail below.

Thus, in an embodiment, the push member 302 includes a proximal portion 344, the central portion 342, and a distal portion 346. The proximal portion 344 of push member 302 includes a proximal end (not shown in FIG. 7) and extends distally to a distal end 348. The central portion 342 includes a proximal end 350 and extends distally in a helix to a distal end 352. The distal portion 346 includes a proximal end 354 and a distal end 356. The proximal end 350 of the central portion 342 is coupled to the distal end 348 of the proximal portion 344. The distal end 352 of the central portion 342 is coupled to the proximal end 354 of the distal portion 344. Thus, the helically-shaped central portion 342 is disposed between the proximal portion 344 and the distal portion 346 of the push member 302, and forms the collar 312. The collar 312 is coupled to the helically-shaped proximal end 306 of the shaft wall 305 of the distal shaft 304. The collar 312 defines the helically-shaped entry port 314 of the distal shaft 304. As explained above, the helically-shaped entry port 314 is configured to provide easy, catch-free, snag-free entry of interventional coronary devices into the passageway 310 of the distal shaft 304.

In an embodiment, the proximal portion 344 of the push member 302 is aligned axially along the second central longitudinal axis LA2, as shown in FIG. 7. In an embodiment, the central portion 342 of the push member 302 is deformed radially and axially, or helically about the first central longitudinal axis LA1 of the distal shaft 304. The central portion 342 is deformed helically such that a helical coil is formed, extending from the proximal end 350 to the distal end 352 of the central portion 342. The distal portion 346 of the push member 302 may be aligned longitudinally with the second central longitudinal axis LA2 of proximal portion 344 of the push member 302. Thus, in an embodiment, the push member 302 extends distally with the proximal portion 344 aligned longitudinally with the second central longitudinal axis LA2, to the central portion 342 forming the collar 312 and extending distally in a helix about the first central longitudinal axis LA1, and continues distally with the distal portion 346 aligned again with the second central longitudinal axis LA2.

As explained above, the push member 302 further includes the push member extension 358, as shown in FIG. 7. The push member extension 358 is disposed between the proximal end 350 and the distal end 352 of the central portion 342. The push member extension 358 includes a proximal end 360 coupled to the push member 302 at the distal end 348 of the proximal portion 344 of the push member 302 and the co-located proximal end 350 of the central portion 342 of the push member 302. The push member extension 358 further includes a distal end 362 coupled to the push member 302 at the distal end 352 of the central portion 342 of the push member 302 and the co-located proximal end 354 of the distal portion 346 of the push member 302. The push member 358 is thus disposed between the proximal portion 344 and the distal portion 346 of the push member 302 along the second central longitudinal axis LA2. The push member extension 358 is configured to transfer motion applied at the proximal portion 344 to the distal portion 346 of the push member 302 along the second central longitudinal axis LA2. More plainly stated, the push member extension 358 is configured to provide pushability to the guide extension catheter 300 over the length of the central portion 342 of the push member 302. In an embodiment, the push member extension 358 is a wire with a generally circular cross-sectional profile. In other embodiments, the push member extension 358 may be any shape suitable for the purposes described herein, such as, but not limited to, a wire with an elliptical, oval, rectangular, or other shaped cross-sectional profile. The push member extension 358 may be formed of materials similar to those of the push member 102, described previously, such as, but not limited to stainless steel, nickel-titanium alloys (e.g. NITINOL), or other suitable materials. The push member extension 358 may be coupled to the proximal portion 344 and the distal portion 346 of the push member 302 by methods such as, but not limited to adhesives, welding, bonding, fusing, mechanical connection, or any other method suitable for the purposes described herein. While the proximal portion 344, the central portion 342, the distal portion 346, and the push member extension 358 of the push member 302 are described herein as separate components, this is not meant to be limiting, and the proximal portion 344, the central portion 342, the distal portion 346, and/or the push member extension 358 may be formed as a single component or in any desired combination of single and co-formed components.

Figure 8:
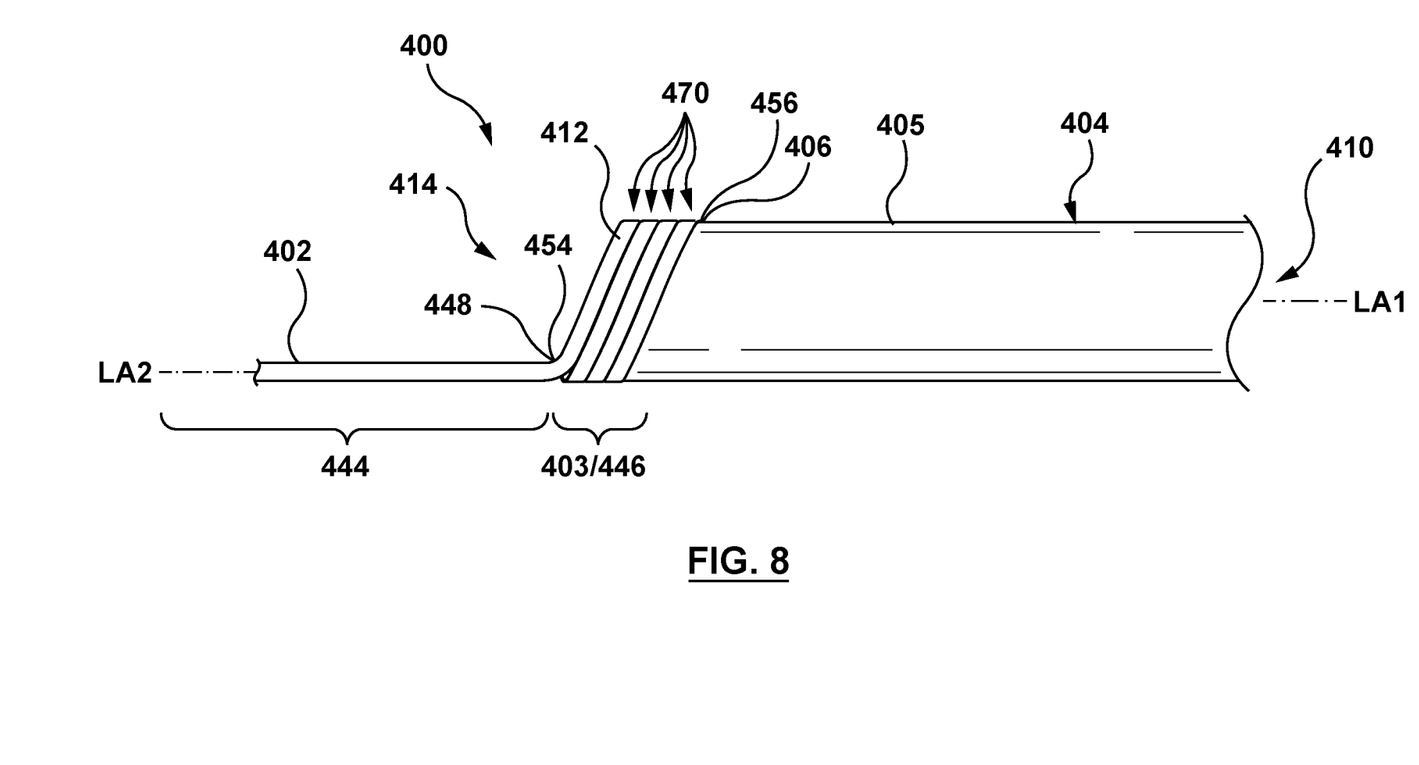
FIG. 8 is a perspective illustration of a portion of a guide extension catheter in accordance with another embodiment hereof.

A guide extension catheter 400 according to another embodiment hereof is illustrated in FIG. 8. The guide extension catheter 400 includes a push member 402, a distal shaft 404, a transition joint 403, a passageway 410 and a collar 412. The guide extension catheter 400 further includes a slanted or angled entry port 414 of the distal shaft. The collar 412 defines the angled entry port 414 of the distal shaft 404. A proximal portion of the push member 402 and the distal shaft 404 are similar to the push member 102 and the distal shaft 104 of the guide extension catheter 100 described previously. Therefore, similarities in construction and alternatives are not repeated with respect to FIG. 8. However, in the embodiment shown in FIG. 8, the collar 414 of the guide extension catheter 400 is formed by a plurality of helical windings 470 of a distal portion 446 of the push member 402.

Thus, in an embodiment shown in FIG. 8, the push member 402 includes a proximal portion 444 and the distal portion 446. The proximal portion 444 of the push member 402 includes a proximal end (not shown in FIG. 8) and extends distally to a distal end 448. The distal portion 446 includes a proximal end 454 and extends distally in a plurality of helical windings 470 to a distal end 456. The proximal end 454 of the distal portion 446 is coupled to the distal end 448 of the proximal portion 444. The distal portion 446 of the push member 402 is configured to form the collar 412, with the collar 412 defining the angled entry port 414 of the distal shaft 404. Thus, the helical windings 470 of the distal portion 446 of the push member 402 form the collar 412 which defines the angled entry portion 414.

In an embodiment, the distal portion 446 of the push member 402 is deformed radially and axially, or helically about a first central longitudinal axis LA1 of the distal shaft 404, as shown in FIG. 8. The distal portion 446 is deformed helically such that the plurality of helical windings 470, also referred to as coils, are formed. The plurality of helical windings 470 extend from the proximal end 454 to the distal end 456 of the distal portion 446 of the push member 402. Thus, the distal portion 446 of the push member 402 forms the collar 412. In an embodiment, the helical windings 470 are formed such that an inner diameter of the helical windings 470 is constant over the length of the helical windings 470 and an outer diameter of the helical windings is constant over the length of the helical windings 470. The collar 412 is coupled to a slanted or angled proximal end 406 of a shaft wall 405 of the distal shaft 404. In an embodiment, each helical winding 470 is coupled to an adjacent helical winding 470. While the example of FIG. 8 shows four (4) helical windings 470 of the distal portion 446 of the push member 402, this is not meant to be limiting, and the distal portion 446 of the push member 402 may include more or fewer helical windings 470. Each helical winding 470 may be coupled to the adjacent helical winding 470 by methods such as, but not limited to adhesives, welding, fusing, bonding, or any other suitable method. Further, although FIG. 8 shows each helical winding 470 in contact with an adjacent helical winding 470, this is not meant to be limiting. Thus, in an embodiment, adjacent helical windings 470 may be spaced from each other.

While the embodiments of FIGS. 1-7 illustrate the helically-shaped entry ports with a specific handedness and pitch, this is not meant to be limiting and the helically-shaped entry ports may be either right of left-handed, and may be of any pitch suitable for the required treatment application. Moreover, the helically-shaped entry ports may be of a constant or a variable pitch. Further, while the embodiments of FIGS. 1-7 include a collar, this is not meant to be limiting. Thus, in some embodiments, the collar may be eliminated such that the helical entry port is formed by the helical proximal end of the distal shaft. In other embodiments, the collar may be integrally formed as part of the proximal portion of the distal shaft. Further, while the embodiment of FIG. 8 shows the helical windings with a specific handedness and pitch, this is not meant to be limiting and the helical windings may be either right of left-handed, and may be of any pitch suitable for the required treatment application.

While only some embodiments have been described herein, it should be understood that it has been presented by way of illustration and example only, and not limitation. Various changes in form and detail can be made therein without departing from the spirit and scope of the invention, and each feature of the embodiments discussed herein, can be used in combination with the features of any other embodiment. All patents and publications discussed herein are incorporated by reference herein in their entirety.

What is claimed is:

1. A guide extension catheter, comprising:
   a push member;
   a distal shaft coupled to the push member and extending distally therefrom, the distal shaft including a shaft wall and a passageway, the shaft wall including a helically-shaped proximal end and a distal end, the helically-shaped proximal end of the distal shaft coiled helically about a first central longitudinal axis of the passageway of the distal shaft, wherein the helically-shaped proximal end defines a helically-shaped entry port of the distal shaft.

2. The guide extension catheter of claim 1, wherein the distal shaft further includes a collar coupled to the helically-shaped proximal end of the shaft wall of the distal shaft, wherein the collar is helically-shaped and defines the helically-shaped entry port.

3. The guide extension catheter of claim 2, wherein the collar is a wire having a generally circular cross-sectional profile.

4. The guide extension catheter of claim 2, wherein the collar is a ribbon having a generally rectangular cross-sectional profile.

5. The guide extension catheter of claim 2, wherein the collar includes a tapered proximal end coupled to the push member.

6. The guide extension catheter of claim 2, wherein the collar includes a tapered distal end coupled to the push member.

7. The guide extension catheter of claim 2, wherein the push member further includes a proximal skive and the collar includes a proximal end coupled to the proximal skive of the push member.

8. The guide extension catheter of claim 2, wherein the push member further includes a distal skive and the collar includes a distal end coupled to the distal skive of the push member.

9. The guide extension catheter of claim 2, wherein the collar is a portion of the push member.

10. The guide extension catheter of claim 9, wherein the push member comprises:
    a proximal portion extending proximally along a second central longitudinal axis of the push member;
    a central portion extending distally from the proximal portion, the central portion deformed helically about the first central longitudinal axis of the passageway of the distal shaft such that the central portion of the push member forms the collar of the distal shaft, the collar coupled to the proximal end of the shaft wall of the distal shaft;
    a distal portion extending distally from the central portion and along the second central longitudinal axis of the push member; and
    a push member extension disposed between the proximal portion and the distal portion of the push member along the second central longitudinal axis, the push member extension coupled to the proximal portion and the distal portion of the push member,
    wherein the push member extension provides pushability to the guide extension catheter over a length of the central portion of the push member.

* * * * *